(12) United States Patent
Kuzma et al.

(10) Patent No.: US 6,757,970 B1
(45) Date of Patent: Jul. 6, 2004

(54) METHOD OF MAKING MULTI-CONTACT ELECTRODE ARRAY

(75) Inventors: Janusz A. Kuzma, Parker, CO (US); William Vanbrooks Harrison, Valencia, CA (US); Lani A. Smith, Parker, CO (US)

(73) Assignee: Advanced Bionics Corporation, Valencia, CA (US)

( * ) Notice: Subject to any disclaimer, the term of this patent is extended or adjusted under 35 U.S.C. 154(b) by 217 days.

(21) Appl. No.: 10/000,408

(22) Filed: Nov. 2, 2001

Related U.S. Application Data
(60) Provisional application No. 60/246,625, filed on Nov. 7, 2000.

(51) Int. Cl.[7] .................................................. H05K 3/02
(52) U.S. Cl. ............................. 29/847; 29/825; 29/846; 600/374; 600/396; 607/126; 607/127
(58) Field of Search ....................... 29/825, 846, 847; 600/374, 396; 607/116, 117, 127

(56) References Cited

U.S. PATENT DOCUMENTS

| | | | |
|---|---|---|---|
| 3,724,467 A | 4/1973 | Avery et al. | 128/418 |
| 3,974,834 A | 8/1976 | Kane | 128/418 |
| 4,106,512 A | 8/1978 | Bisping | 128/418 |
| 4,284,856 A | 8/1981 | Hochmair et al. | 179/107 |
| 4,357,497 A | 11/1982 | Hochmair et al. | 179/107 |
| 5,097,843 A | 3/1992 | Soukup et al. | 128/784 |
| 5,239,999 A | 8/1993 | Imran | 128/642 |
| 5,267,564 A | 12/1993 | Barcel et al. | 128/634 |
| 5,423,763 A | 6/1995 | Helland et al. | 604/174 |
| 5,456,707 A | 10/1995 | Giele | 607/127 |
| 5,458,629 A | 10/1995 | Baudino et al. | 607/116 |
| 5,833,714 A | 11/1998 | Loeb | 607/56 |
| 6,070,105 A | 5/2000 | Kuzma | 607/137 |
| 6,112,124 A | 8/2000 | Loeb | 607/137 |
| 6,129,753 A | 10/2000 | Kuzma | 607/137 |

*Primary Examiner*—Carl J. Arbes
(74) *Attorney, Agent, or Firm*—Bryant R. Gold

(57) ABSTRACT

A multicontact electrode array suitable for implantation in living tissue includes a distal end having multiple spaced-apart ring contacts or a pattern of spaced-apart electrode contacts carried on a flexible carrier. Each electrode contact is resistance welded to a respective wire that is wound helically inside a silicon tube. The center of the helix defines a lumen wherein a positioning stylet, or other suitable positioning tool, may be removably inserted when the electrode array is implanted. The electrode array is made using a method that includes, as an initial step, winding lead wires around a suitable mandrel forming a helix configuration. Next, a non-conductive silicone tube jacket is placed around the wound wires, exposing the distal lead ends of the wires at a distal end of the tube. A welding process is then used to bond each wire tip to a corresponding metal electrode contact which has been preassembled by resistance welding to a metal foil structural carrier. The electrode array, including the metal foil structural carrier, is then formed into a tube by drawing it through a die. The excess foil material at the distal tip is then trimmed and a heat-shrink tube is placed around the assembled foil tube to prevent leakage of the polymer filler material through the joining longitudinal line of the carrier. Next, the foil tube is injected with a polymer filler material to void any gaps between the lead wires and contacts. To avoid filling the central lumen with the polymer filler material, a central core or stylet is temporarily placed inside the lumen. The heat-shrink tube is then mechanically removed. The fabrication method is finalized by inserting the preassembled electrode array into a hot acid mixture, which etches away the metal foil carrier, exposing the contacts at the surface of a distal end of the electrode array.

22 Claims, 11 Drawing Sheets

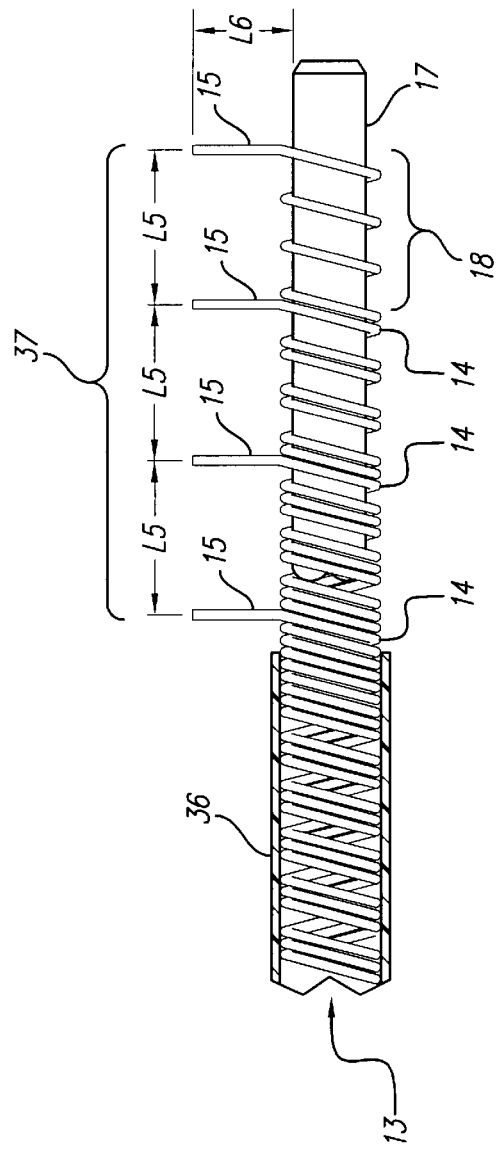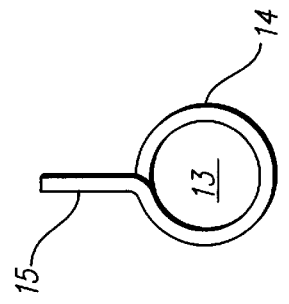
FIG. 6A
FIG. 6B

METHOD OF MAKING MULTI-CONTACT ELECTRODE ARRAY

The present application claims the benefit of U.S. Provisional Application Serial No. 60/246,625, filed Nov. 7, 2000, which application is incorporated herein by reference.

BACKGROUND OF THE INVENTION

The present invention relates to the field of implantable electrodes, and more particularly to a multicontact electrode array. In a preferred embodiment, such multicontact electrode array is used with an implantable stimulator to provide electrical stimulation to body tissue, for example, to brain tissue for brain stimulation, to selected nerves for neural stimulation, or to the spinal cord for spinal cord stimulation (usually done to control or manage pain). Additionally, the present invention further provides a simple and reliable method of constructing a multicontact electrode array.

Spinal cord and other stimulation systems are known in the art. For example, U.S. Pat. No. 3,724,467, teaches an electrode implant for the neuro-stimulation of the spinal cord. A relatively thin flexible strip of physiologically inert plastic is provided as a carrier on which a plurality of electrodes is formed. The electrodes are connected by leads to an RF receiver, which is also implanted, and which is controlled by an external controller.

In U.S. Pat. No. 5,458,629, a method of making an implantable ring electrode is taught. The method disclosed in the '629 patent describes an electrode array with a first lumen containing electrical conductors and a second lumen adapted to receive a stylet. In contrast, the multicontact electrode array of the present invention requires only one lumen, and thus the fabricating steps described in the '629 patent differ from those taught by the present invention. Moreover, the '629 patent teaches that notches must be formed in the lead body to position the electrode members, whereas the present invention does not require such notches.

Other implantable electrodes, electrode arrays, and features of implantable electrodes are taught, e.g., in U.S. Pat. Nos. 5,097,843 (a porous electrode); 5,267,564 (a built-in sensor); 5,423,763 (a suture sleeve for anchoring the lead body); 5,447,533 (a combination electrode and drug delivery system); 5,466,253 (a crush resistant multiconductor lead body); 4,819,647 (a spirally-shaped electrode array); 5,833,714 (electrodes made from tantalum); 6,112,124 (electrodes separated by dielectric partitions or fins); 6,070,105 (modiolus-hugging electrodes for insertion into the cochlea); and 6,129,753 (electrode array with contacts on medial side for insertion into cochlea). Still other electrodes are taught in U.S. Pat. Nos. 4,284,856; 4,357,497; and 6,125,302; or in PCT Publication WO 00/71063A1. The materials from which an implantable electrode array is made in accordance with the teachings of these patents, including many of the manufacturing techniques disclosed in these patents, may also be used with the present invention. For that reason, the patents listed in this paragraph are incorporated herein by reference.

Despite the various types of implantable electrode arrays known in the art, significant improvements are still possible and desirable, particularly relating to reducing costs and providing a more reliable construction based on new manufacturing technology.

Most designs of electrodes and connectors, for example, are based on the principle of molding a contact or array of contacts, usually made from biocompatible metal, into a polymer carrier, such as silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required. One of the main problems encountered in the fabrication of such electrodes or connectors is to find a reliable method of holding the system of contacts in the desired and stable position during the process of welding connecting wires and during the process of molding the polymer carrier. A further problem relates to maintaining a controlled surface of the contacts that are to remain exposed, i.e., to ensure that the contacts are not covered by the polymer when the carrier is molded.

It is thus seen that there is a continual need for improved, more reliable, implantable multicontact electrode arrays that are simpler to make and less costly to make.

SUMMARY OF THE INVENTION

The present invention addresses the above and other needs by providing a simple and reliable method of constructing a multicontact electrode array.

The present invention focuses on the construction of the distal end of the electrode array where the electrodes are positioned in a specified spaced-apart relationship.

The invention disclosed and claimed herein provides a simple and reliable method of construction for a multicontact electrode array. Advantageously, during the construction of such electrode, a central lumen is formed in the electrode array lead body. This lumen serves the purpose of providing access for a stylet to be used in conjunction with the lead during implantation of the electrode to the stimulating area. The electrode array may be constructed to have various ring contacts, partial rings, or radially spaced pattern of small contacts of any shape. Depending on the application for which the electrode array is to be used, e.g., brain stimulation, neural stimulation, or spinal cord stimulation the number of contacts will vary. Most of the electrode arrays used for such applications employ between 4 and 16 electrodes, and the arrangement of the electrodes can vary. For example one known arrangement is the paddle type electrode array. Electrodes of the paddle type array, are arranged in two or more parallel columns, permitting stimulation to be driven across an adjacent electrode. Another type of known arrangement positions the electrodes in a row, or "in line," along the longitudinal axis of a small diameter lead body. This in-line electrode arrangement allows the array to be inserted into the stimulating area, in a minimally invasive procedure, through the use of a large diameter needle and through the guidance of a stylet inserted in the lumen of the electrode array.

The present invention is directed to an electrode array wherein the electrodes are organized in a row, "in line," or in a radially placed pattern of small contacts of any shape, and more particularly to a method of construction for making such electrodes. The simplified construction method provided by the invention advantageously reduces material costs, simplifies manufacturing processes, and thus reduces manufacturing time and labor costs.

The method of making an electrode array in accordance with the present invention includes, as an initial step, winding insulated lead wires around a suitable mandrel forming a helix configuration. Helically-wound wire may also be purchased from a vendor. Next, a non-conductive silicone tube jacket is placed around the wound wires exposing the distal lead ends of each insulated wire. A welding process is then used to bond each lead wire tip to a corresponding contact which has been preassembled by resistance welding to a metal foil, e.g., iron foil, structural carrier. The electrode array is then molded after drawing it through a die. The excess foil material at the distal tip is then trimmed, and a heat-shrink tube is placed around the assembled electrode array to prevent leakage of an injected polymer through the small gap of the joining longitudinal line of the foil carrier. The electrode array is then injected with a polymer material to fill any gaps between the lead wires and contacts. To avoid filling the central lumen with the polymer filler material, a central core or stylet is temporarily placed inside the lumen. The heat-shrink tube is then mechanically removed. The construction method is finalized by inserting the preassembled electrode array into a hot acid mixture which etches away the iron foil exposing the contacts at the surface of the electrode array.

The construction method of the present invention is more simplified than others known in the art, and hence provides a more reliable construction method with higher yield rates. All this, in turn, lowers the overall cost to manufacture the multicontact electrode array.

BRIEF DESCRIPTION OF THE DRAWINGS

The above and other aspects, features and advantages of the present invention will be more apparent from the following more particular description thereof, presented in conjunction with the following drawings wherein:

FIG. 6A depicts the preparation of the multiwire lead by helically winding multiple wires around a suitable mandrel and leaving the distal ends of the wires pointing radially away from the mandrel;

FIG. 6B shows an end view of the multiwire lead;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches a manufacturing technique for an implantable electrode array having multiple ring contacts, partial rings, or a pattern of radially placed small contacts of any shape. Typically, each contact is evenly spaced along the longitudinal axis of the lead, although unevenly spaced contacts could also be made.

Figure 1:
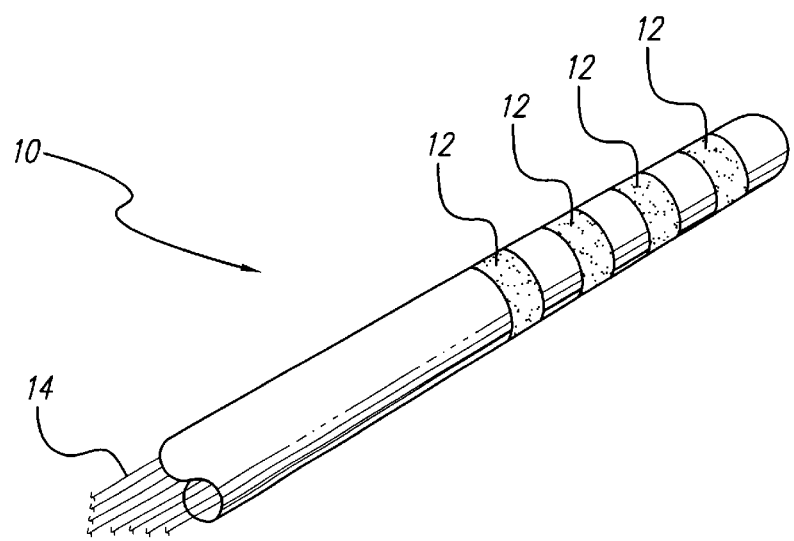
FIG. 1 shows a perspective view of a preferred embodiment of a multicontact electrode array with ring contacts.

FIG. 1 shows a preferred embodiment of an electrode array 10 with four ring contacts 12 made in accordance with the invention. The number of contacts can vary depending on the purpose for which the electrode array is to be used. The electrode array of the present invention may be used with any suitable implantable neural stimulator or pulse generator, and may have as few as one contact, or as many as 30 contacts, or more. Typically, for most applications, the number of contacts will vary from two to eight.

Figure 2:
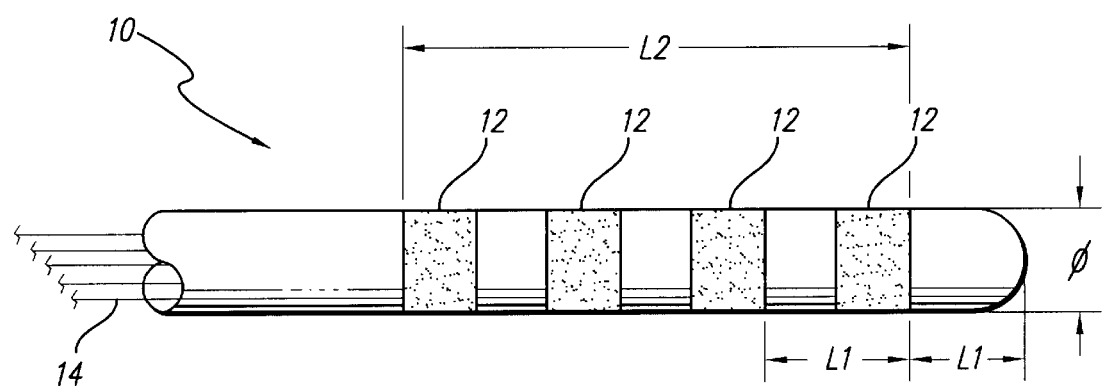
FIG. 2 is a side view of the preferred embodiment shown in FIG. 1.

As seen in FIG. 1, a partial perspective view of the electrode array 10 is shown with four ring contacts 12. Not shown in FIG. 1 (but present as will be apparent from the description that follows) are four corresponding laser spot welds where four respective insulated lead wires are electrically connected to the ring contacts. FIG. 2 shows the location of the four ring contacts spaced a distance L1 from the distal tip of the electrode array 10 and having a total distance L2, where representative values for L1 and L2 are, 2.0 mm and 8.0 mm, respectively. The outside diameter, ø, is also shown in FIG. 2. In a representative embodiment, ø=1.2 mm.

Figure 5:
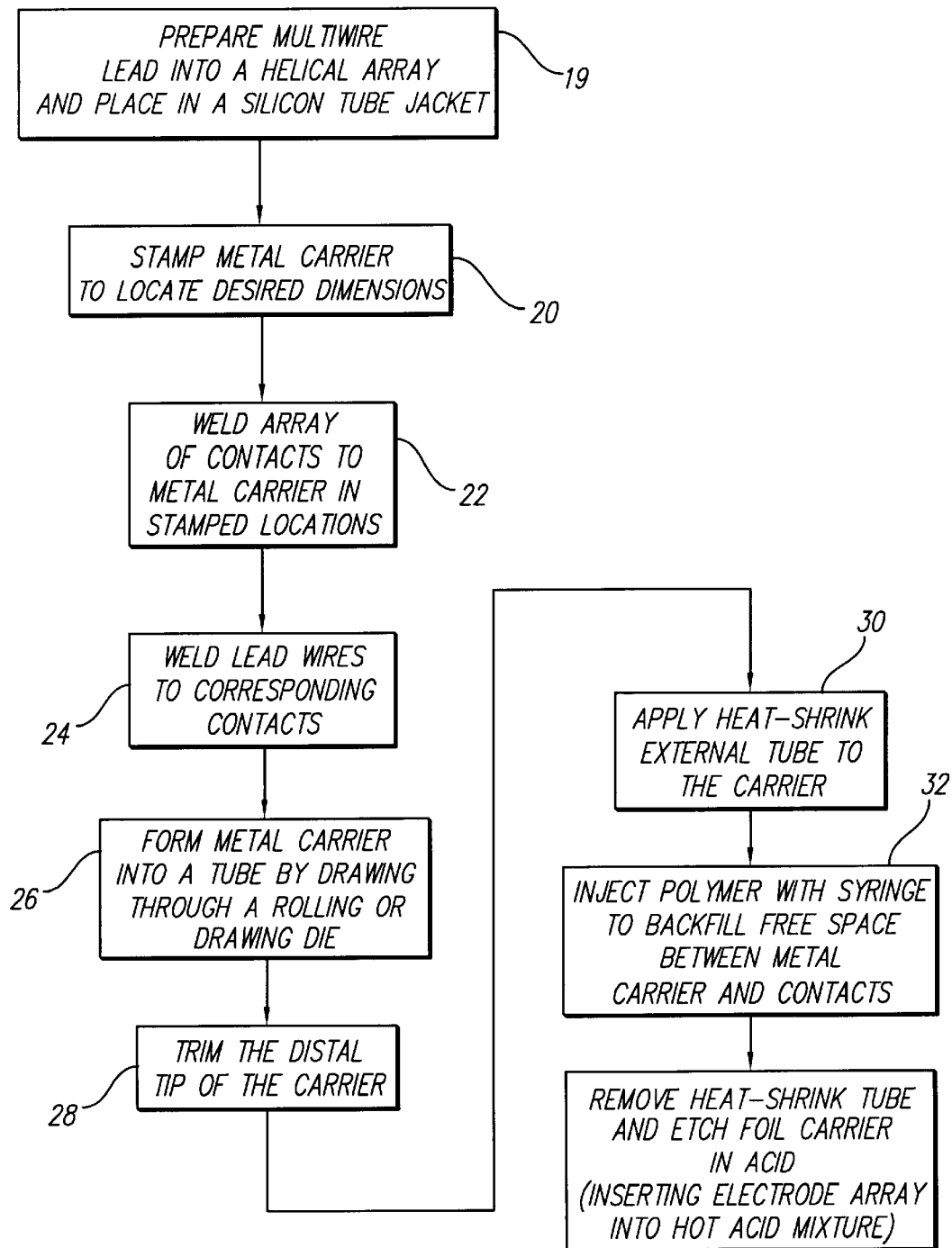
FIG. 5 shows a flow chart diagram that illustrates the manufacturing steps used to make the electrode array shown in FIG. 1.

The manufacturing technique or method used in making the electrode array 10 is identified in FIG. 5. Each manufacturing step shown in FIG. 5 will be explained in detail below. Advantageously, the process is a simple and reliable technique that can be carried out using simple materials, processes, and equipment, and when used provides a high manufacturing yield rate. Because the method is relatively easy to use and relatively inexpensive, it allows a ring type, partial ring, or a pattern of radially placed small contacts to be assembled as part of the multicontact electrode.

The simple process and preferred method of making the electrode array 10 is best understood in connection with the description of the flow diagram shown in FIG. 5. Significant features of the multicontact electrode are further shown in FIGS. 6A through 15.

Most designs of electrodes and connectors are based on the principle of molding a contact or array of contacts, usually made from biocompatible metal, into a polymer carrier, such as silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required. One of the main problems encountered in the fabrication of such electrodes or connectors is to find a reliable method of holding the system of contacts in the desired and stable position during the process of welding the connecting wires and during the process of molding the polymer carrier. A further problem relates to maintaining a controlled surface of the contacts that are to remain exposed, i.e., to ensure that the contacts are not covered by the polymer when the carrier is molded.

The preferred method of making the electrode array 10 described below in connection with FIGS. 5 through 15 is based on the principle of attaching (e.g., by the process of resistance welding) electrode contacts made from precious, biocompatible material (such as platinum or its alloys) to a metal foil carrier made from an iron strip or similar etchable metal or metal alloys. The lead wires, also typically made from platinum or titanium, or alloys thereof, are also attached (e.g., by the process of resistance welding) to the electrode contacts. Resistance spot welding advantageously provides a secure electrical attachment of the electrode material to the insulated wire and also assures a secure mechanical attachment of the electrode material to the foil carrier.

To illustrate the manufacturing method, such method will be described relative to the fabrication of the preferred embodiment electrode array 10 shown in FIG. 1. With reference to FIG. 5, a flow diagram identifying the steps of the manufacturing process of the electrode array is depicted. As an initial step 19, a multiwire lead is formed into a helical array. That is, multiple number of insulated lead wires 14, as shown in FIG. 6A, are wound around a mandrel 17, in a multihelix orientation 18. Each lead wire 14 is wound around the mandrel 17 separately leaving an excess distance L6 at the initial contact point. (This initial contact point, as will be evident from the description that follows, represents the distal end 15 of the wire 14 and electrode array 10. The excess wire that extends out from the mandrel the distance L6 may also be referred to as a "pigtail".) The distance L6 must be greater then about 0.5 mm since the wire tip 15 will eventually be spot welded to the contacts. The starting point of the second wire will be after the third helix turn of the first wire a distance L5, where L5, for the example shown in FIG. 6A, is 2.0 mm. Each successive wire will then follow the same pattern until enough lead wires 14 are represented for the required number of ring contacts in the electrode array. (The spacing distance L5 should be the same as or close to the same spacing as the contact spacing.) As an example, FIG. 6A shows a section of four lead wires 14 wound in a helix pattern 18. The mandrel 17 is used to support the orientation of the wires and for forming a lumen 13 in the longitudinal axis of the helical wound wires. The formed central lumen 13 is used for the purpose of directing or positioning the electrode array 10 into the stimulating area using an insertion stylet or other similar instrument as is known in the art of positioning electrode arrays. The wires 14 are wound in multihelix manner for the full length of the lead body (not shown), thereby defining the lumen 13 along the full length of the lead. The helical wound lead wires 14 are then placed inside a round tube jacket 36 as shown in FIG. 6A. The tube jacket 36 is made from any suitable non-conductive material, such as silicone. The tube jacket 36 extends the full length of the lead wires 15, only section 37 of the wound lead wires is exposed. The lead wire section 37 contains the excess portions of the lead wires 15 (or pigtail ends), which are welded to the contacts 12 during a subsequent step of the manufacturing process, as explained below. FIG. 6B shows an end view of the lead wire and its protruding "pigtail" end tip 15.

Figure 7:
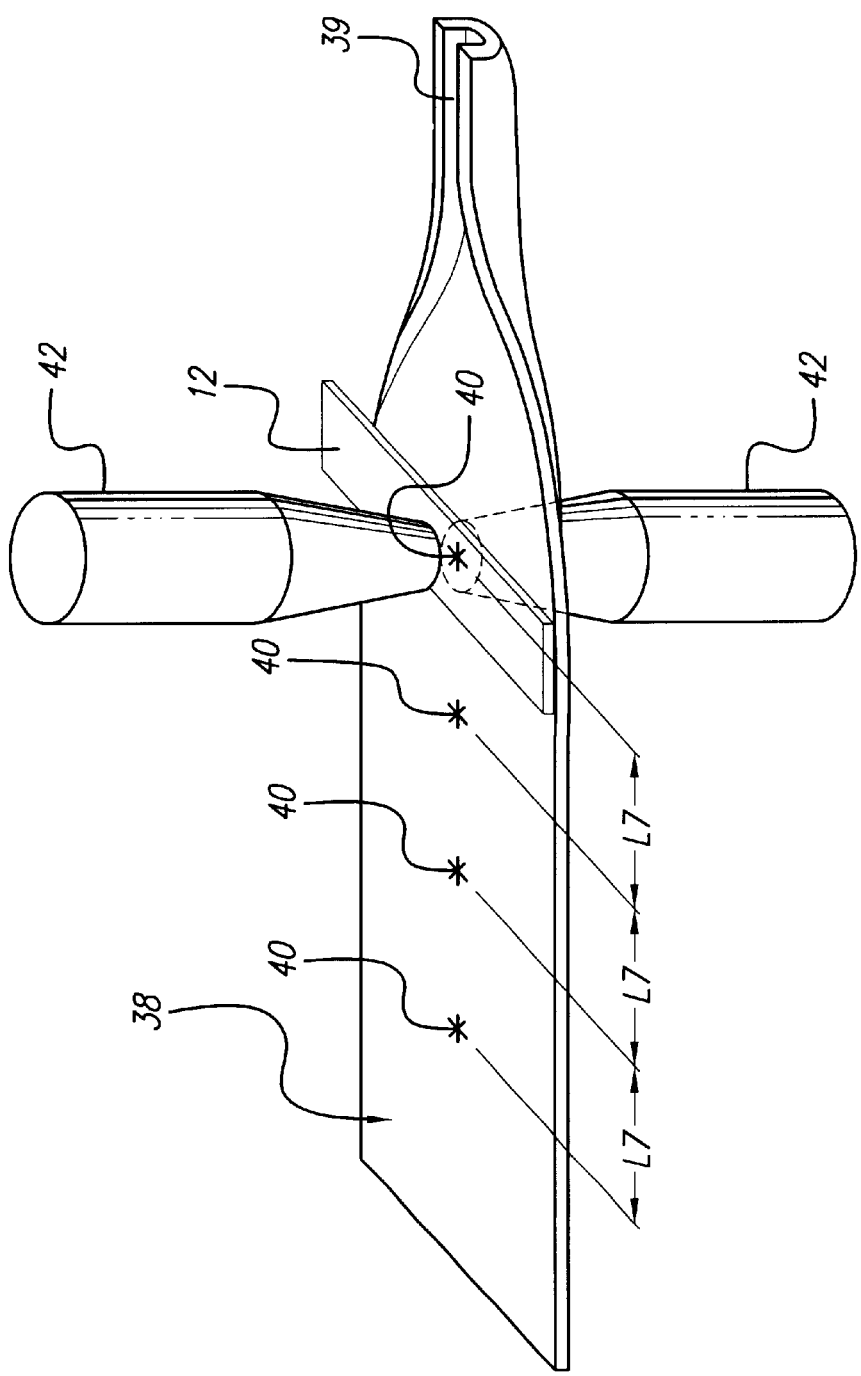
FIG. 7 depicts one method of spacing the electrode contacts to the iron foil.

The next step 20 shown in FIG. 5, requires pre-welding the contacts to the iron foil in the desired spacing using a spacing tool or similar tool, and then trimming the metal foil carrier 38 to make the desired locations where the electrode contacts are to be positioned. FIG. 7 shows the pre-weld location 40 of the metal foil carrier 38 using a welding tool 42. The locations are spaced a distance L7 apart, which for the example shown is 2.0 mm (other desired spacing could, of course, also be used). The distal end 39 of the carrier is folded as shown in FIG. 7 to allow the assembled electrode array to be positioned into a drawing die during a subsequent step of the manufacturing process.

Figure 8:
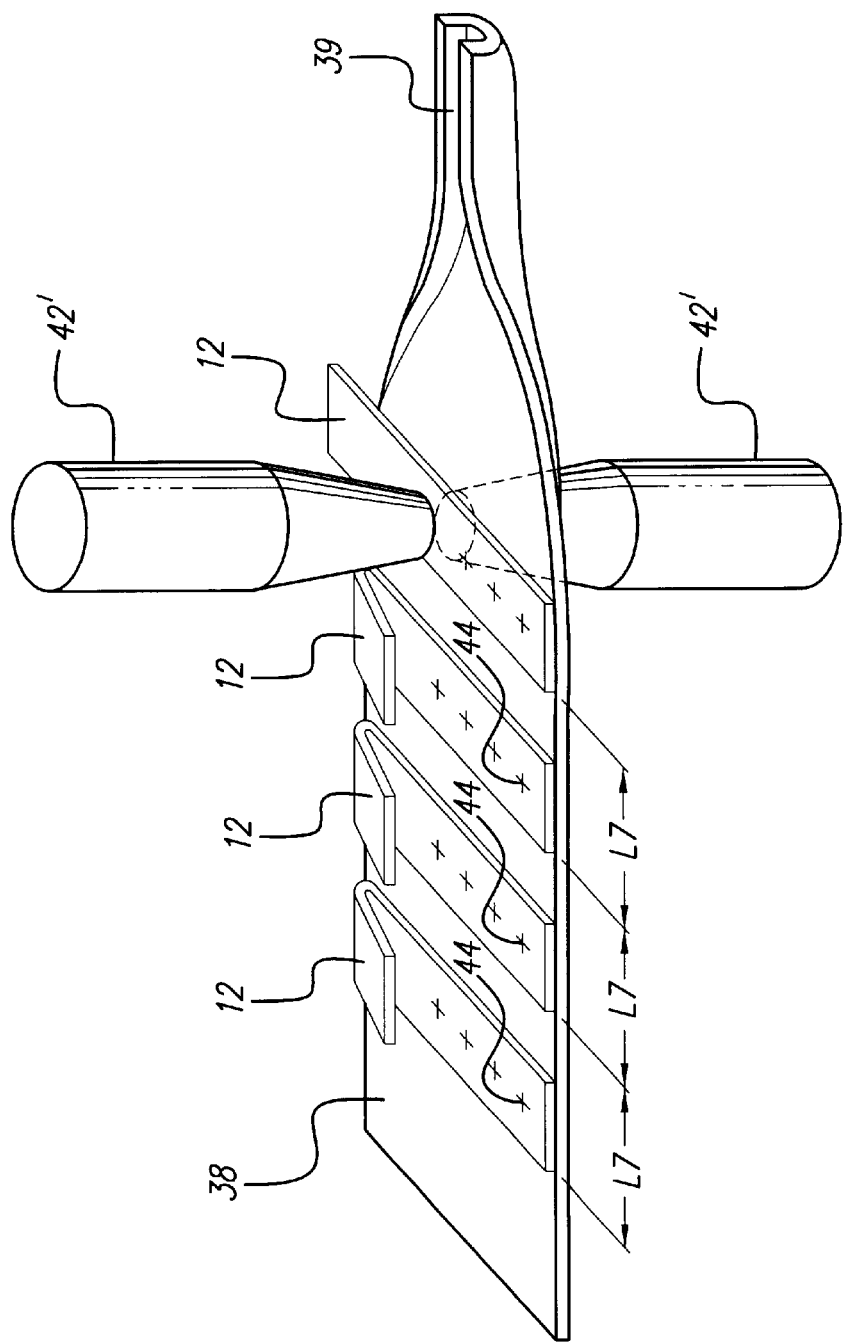
FIG. 8 illustrates a welding process used to weld the platinum electrode contacts to the iron carrier.

The next step 22 shown in FIG. 5 involves welding the array of contacts to the metal foil carrier in the designated locations. The electrode contacts 12 are made from precious, biocompatible material (such as platinum or its alloys). FIG. 8 shows the contacts 12 welded onto an iron foil carrier 38 at various locations 44 using a welding tool 42' for the entire length of the iron carrier. Resistance welding advantageously provides a secure attachment of the electrode material to the foil carrier without causing a deep fusion of the two materials being attached. The resulting shallow fusion contact, in turn, allows clean exposed electrode surface areas to be formed when the iron foil carrier is chemically etched away, as explained in more detail below. Other types of attachment that result in shallow fusion of the electrode material and the foil carrier sheet material may also be used in lieu of resistance welding.

When the contacts 12 are being welded, they are spaced apart a distance L7, which for the example shown in FIG. 8, is 2.0 mm. Other distances could be used, as desired. One end of the contact 12 is folded as shown in FIG. 8. The function of the fold is to hold the lead wire tip 15 in place during the welding process of the insulated lead wire to each corresponding contact. Advantageously, such fold forms a sandwich configuration that achieves a reliable electrical and mechanical connection. This welding process becomes the next step 24 in the manufacturing process of the electrode array 10 identified in FIG. 5.

Figure 9:
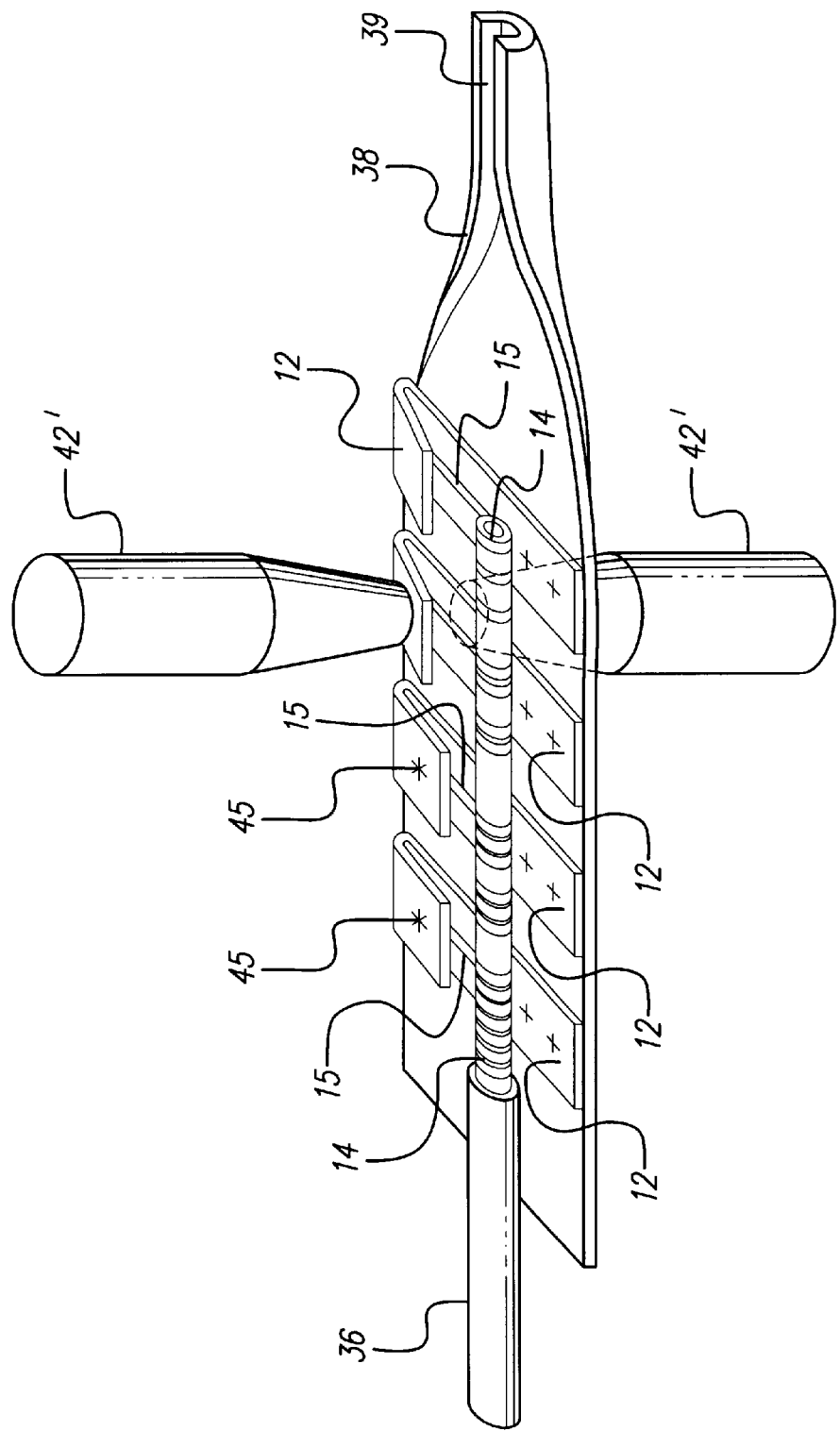
FIG. 9 illustrates the welding process used to bond the lead wires to the corresponding platinum electrode contacts.

Referring momentarily to FIG. 9, the lead wire tips 15 are shown welded in between the fold of the contacts 12 using the same welding process as explained above at locations 45 using the welding tool 42'. The embodiment shown in FIG. 9 shows the connection of four contacts 12 and four lead wire tips 15, but the required amount of connections between the contacts and the lead wires depends on the length of the electrode array and its intended purpose. There could be as few as one connection and as many as thirty (or more) in the manufacturing process of the electrode array. Preferably, all required ring contacts are the same.

Here, it should be noted that the contacts 12 shown in FIGS. 8 and 9, which comprise strips of a biocompatible precious metal, are used to form ring electrodes in the finished array. Other shapes of metal contacts may also be used, as desired, to form other types of electrodes, e.g., partial ring electrodes, radially-pattern spot electrodes, or the like.

Figure 10:
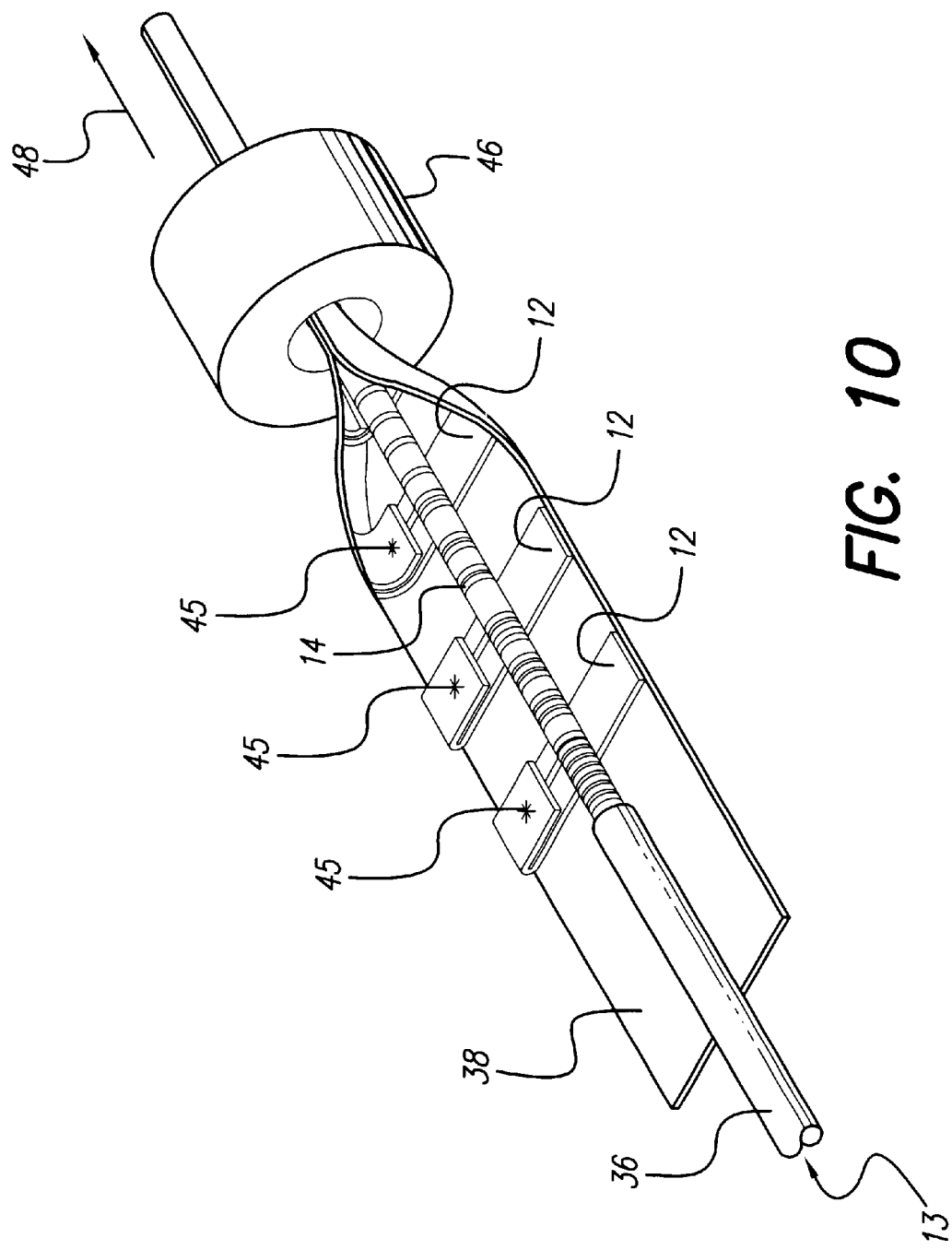
FIG. 10 shows the assembly of FIG. 9 inserted into a drawing die.
Figure 11:
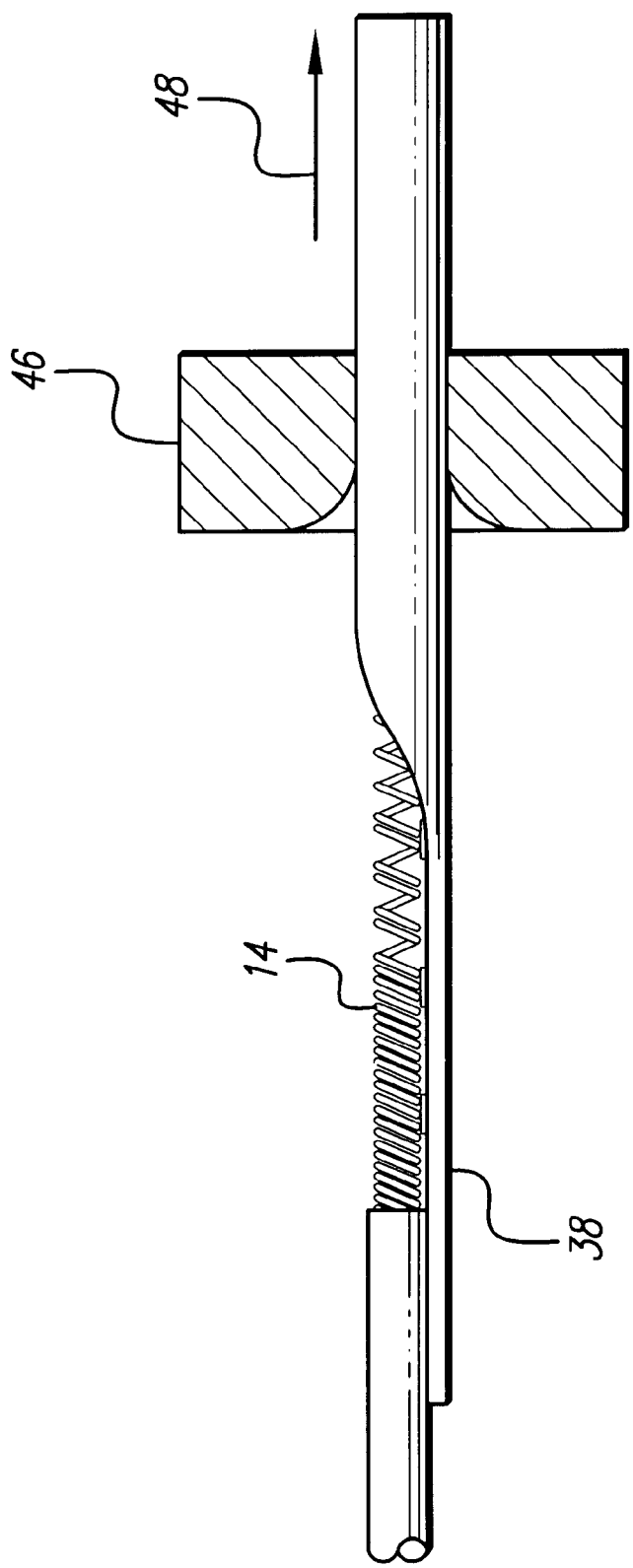
FIG. 11 shows a side view of FIG. 10, representing a preferred method to draw the electrode array using a die.

With reference next to FIGS. 10 and 11, the electrode assembly is shown being inserted into a drawing die 46. This manufacturing step is described in box 26 of FIG. 5. The metal carrier 38 is formed into a tube by drawing the carrier through the die 46. To avoid closing the central tunnel during the molding process, a core or stylet should be inserted into the lumen 13 in the direction shown by the arrow 48. The molded tube then assumes a round or elliptical cross-sectional shape and is straight or gently curved along its longitudinal axis.

Figure 12:
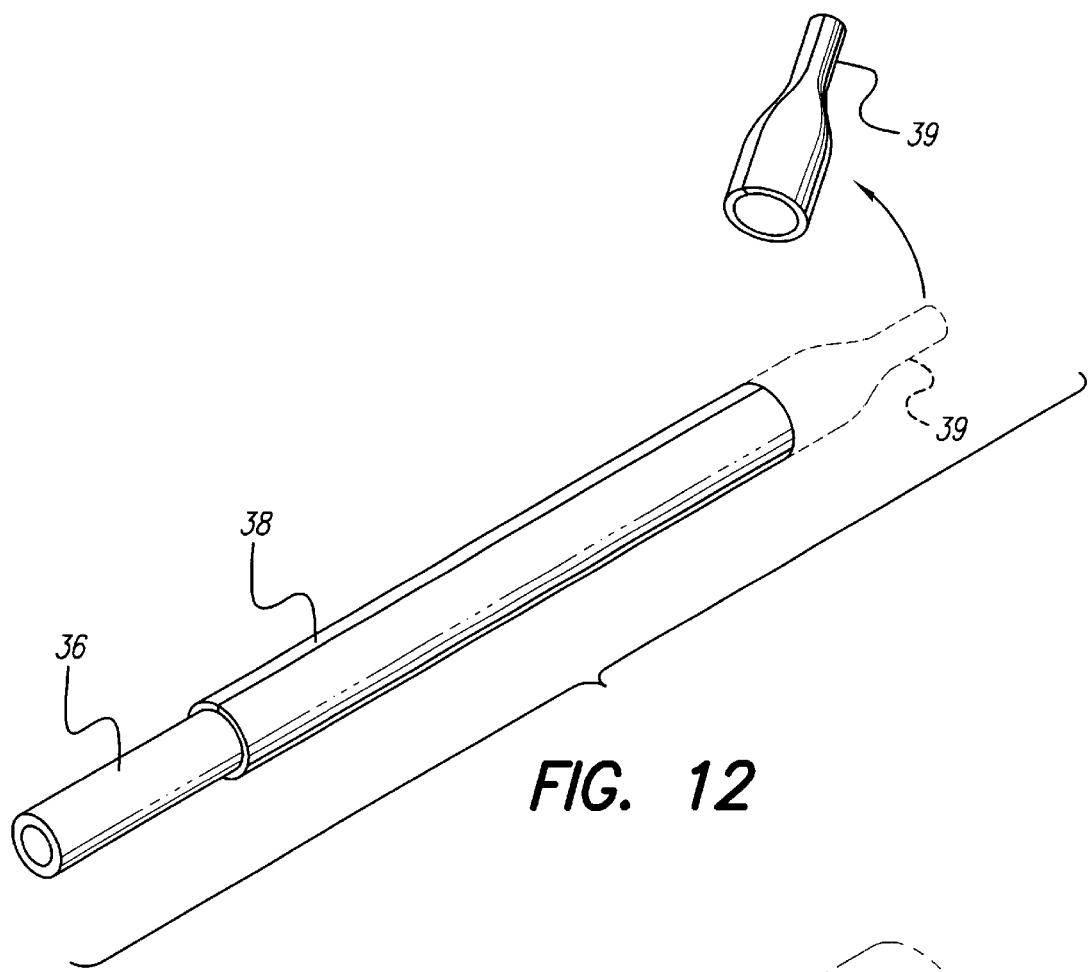
FIG. 12 shows a perspective view of the carrier trimmed at the distal tip used for pulling the carrier through the die.
Figure 13:
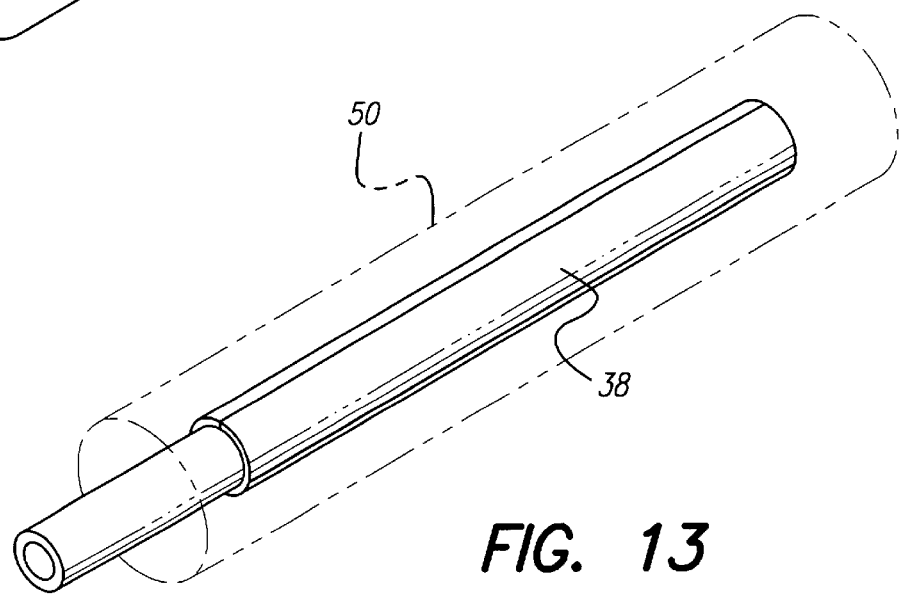
FIG. 13 illustrates the placement of a shrink tube over the electrode assembly.

Once the assembly of the electrode array has been molded, or pulled through the center of the drawing die 46, the deformed distal tip 39 of the carrier is trimmed as shown in FIG. 12 to create non-obstructive access for polymer injection. Trimming the distal tip 39 of the carrier 38 is identified as step 28 in FIG. 5. The trimming step 28 is essential to create access for polymer flow during the injection of the polymer filler material.

After the distal tip 39 of the electrode array 10 has been trimmed, a heat-shrink external tube 50, made from silicon, is applied as indicated in step 30 of the manufacturing process shown in FIG. 5. The phantom lines shown in FIG. 13 identify the heat-shrink external tube 50 that is slid over the electrode assembly. Heat is applied to the tube 50, causing it to shrink and tightly engage the electrode array 10. The heat-shrink external tube 50 is used to prevent leakage of the injected polymer through the small gap along the joining longitudinal line of the foil carrier.

Figure 14:
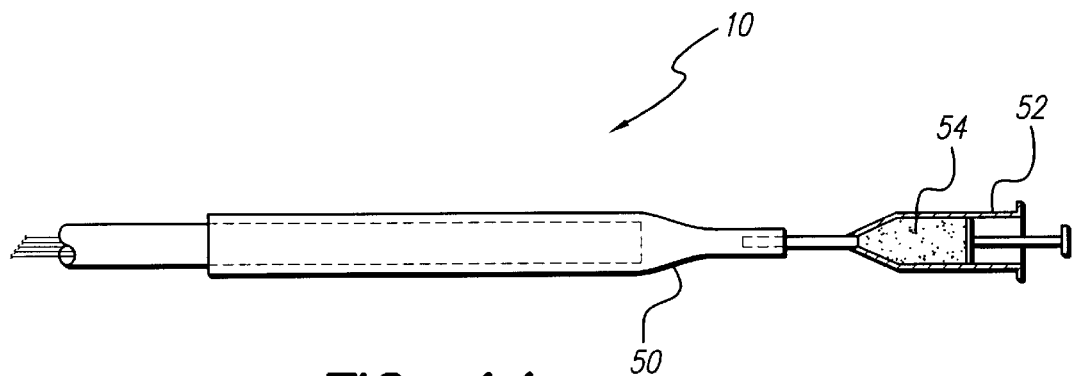
FIG. 14 shows a side view of the assembled electrode and illustrates the use of a backfilling polymer syringe to fill in the gaps formed by the lead wires and contacts.

Next, with reference to FIG. 14, a side view of the electrode array 10, heat shrink tube 50, and syringe tool 52 is shown. During manufacturing step 32 shown in FIG. 5, a syringe tool 52 containing a supply of a polymer filler material 54 is used to inject the polymer filler material into the distal end of the electrode array. To avoid filling the central lumen 13 with the polymer filler material, a central core or stylet may be inserted during the process of injecting the polymer filler 54. The polymer filler 54 is injected into the electrode array for the purpose of filling any gaps which may exist between the lead wires 14 and the contacts 12. When the required amount of polymer filler material has been injected, the polymer is then allowed to cure in a conventional manner. A suitable filler material, for example, is a type of silicone polymer known as LSR-70. The properties of LSR-70 are well known in the art, and LSR-70 may be obtained commercially from numerous sources. LSR-70 is formed into a desired shape by injecting or otherwise inserting it into a mold while in a liquid state and allowing it to cure in the mold at a specified temperature for a specified time period.

After the filler material 54 (e.g., LSR 70) has been injected and cured, the shrink tubing is mechanically removed. For example, the shrink tubing is removed by cutting with a scalper or similar tool and then peeling it off. Then follows the etching process depicted in box 34 of FIG. 5. Chemical etching involves the use of a mixture of diluted acids, such as $HNO_3$ and HCI. The most important part of etching is to control how much material is etched away. Various parameters known in the art of etching are controlled, such as the concentration of the acid mixture, the time involved during the etching insertion, the method of application, and the temperature. The temperature is generally a critical factor because, typically the higher the temperature, the faster the etching rate becomes. It is also known in the art of etching that iron dissolves early in the hot acid mixture as opposed to platinum or its alloys which mechanically stay attached. In a preferred process, after diluting with distilled water, the concentration for $HNO_3$ is about 20% and for HCI the concentration is about 5%; the acid mixture is then heated to about 90° C.; and the etching process takes about five minutes.

Figure 15:
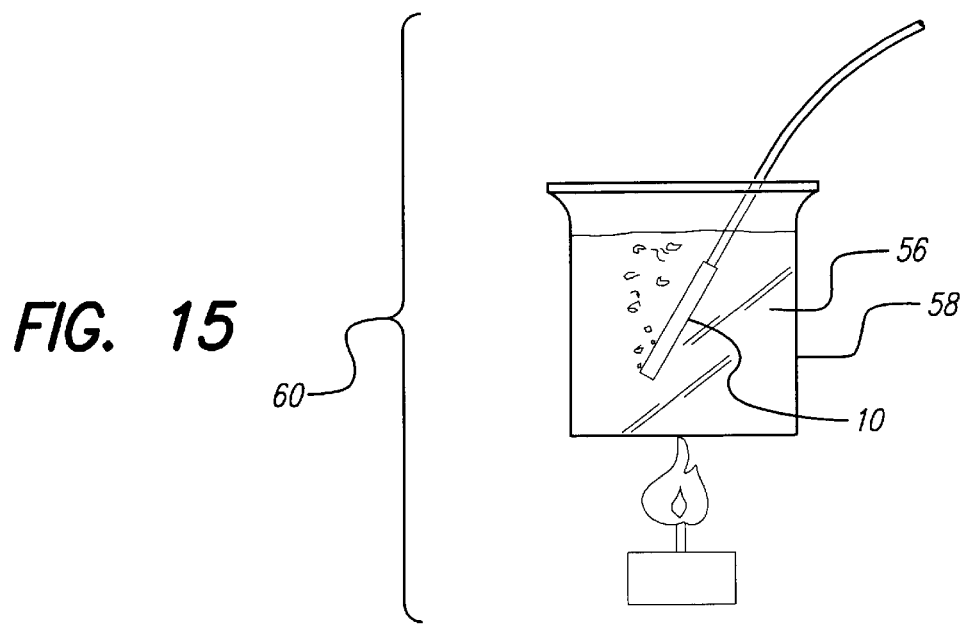
FIG. 15 shows the etching process of inserting the assembled electrode in a hot acid mixture.

FIG. 15 schematically illustrates one method that could be used for the etching process 60 for this invention. This method consists of heating the acid mixture 56 in a laboratory container 58 and inserting the electrode array 10 into the heated acid mixture for a specified time, typically one to three minutes depending on the concentration of the acid and the temperature. Upon insertion into the acid, the metal foil carrier 38 is chemically etched away, leaving the precious metal contacts 12 exposed. The contacts 12 and polymer 36 and 54 are immune to the acid and remain intact and are held in place by the backfilled polymer, in their unaltered shape, and thereby provide the desired electrode array structure. The electrode array structure may then be examined to quality standards.

Figure 3:
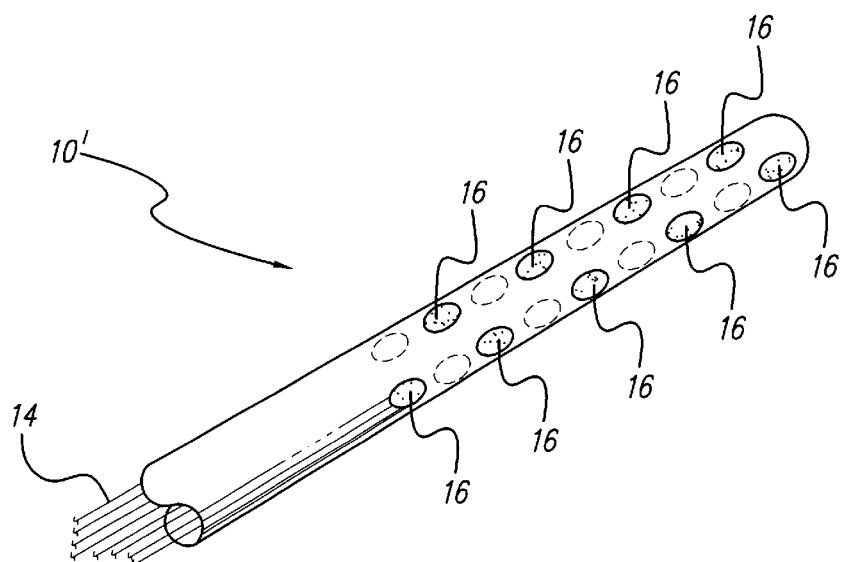
FIG. 3 shows a perspective view of an alternate embodiment of a multicontact electrode array having a pattern of radially spaced small contacts.
Figure 4A:
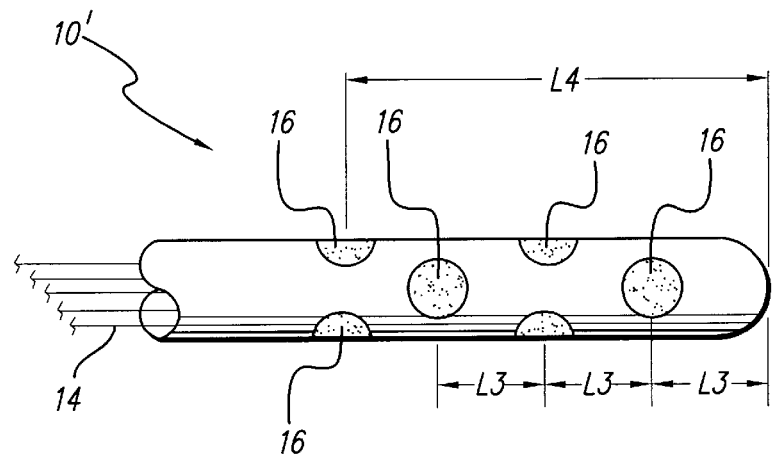
FIG. 4A is a side view of the alternate embodiment shown in FIG. 3.
Figure 4B:
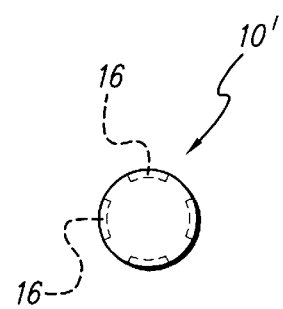
FIG. 4B is a front view of the alternate embodiment shown in FIG. 3.

The manufacturing method of the present invention, identified in FIG. 5, consists of the steps shown. This method has been described in conjunction with FIGS. 6A–15. One preferred embodiment of a manufactured electrode array 10 is shown in FIGS. 1 and 2. In addition, an alternative embodiment of an electrode array 10' made in accordance with the present invention is shown in FIGS. 3, 4A and 4B. This alternative electrode array 10' is the same as the array 10 illustrated in FIGS. 1 and 2 with the exception of the contact shape. In the alternative embodiment, a pattern of radially spaced small contacts 16 are welded as opposed to ring contacts 12. The shape and the number of the contacts 16 can vary. An example of elliptically-shaped contacts is shown in FIG. 3. FIG. 4A shows the longitudinal location of eight contacts with a distance L3=2.0 mm and L4=8.0 mm. FIG. 4B shows the radial location of the contacts. It is to be understood that these dimensions, as well as other dimensions presented herein, are only exemplary of one embodiment, and are not meant to be limiting. The same manufacturing process identified in FIG. 5 can be used to build the radially oriented electrode 10' shown in FIG. 2. In FIG. 2, the array of disk contacts 16 may be welded to the iron foil carrier 38 and spot welded to preselected lead wires 14. For high-density electrodes, the contacts can be formed as flamed balls on the protruding ends 15 of the lead wires 14 and welded directly to the foil carrier 38.

The proximal end of the manufactured electrode array may include a connector to allow the wires 14 to be detachably electrically connected to a suitable pulse generator (not shown in the drawings). Alternatively, the proximal end of the wires 14 may be connected to a feedthrough pin, or other electrical contact point included in or on the pulse generator, in conventional manner, without the use of a detachable connector.

As described above, it is thus seen that the present invention provides an electrode array that is easy to manufacture and which provides enhanced performance when used due to the alignment between the lead wire and contacts. Such electrode provides an array of spaced-apart ring contacts, partial rings, or a pattern of radially-placed small contacts along its longitudinal axis. The simple and reliable construction method of the described electrode array makes this invention a very cost-effective approach for manufacturing such a multicontact electrode array.

While the invention herein disclosed has been described by means of specific embodiments and applications thereof, numerous modifications and variations could be made thereto by those skilled in the art without departing from the scope of the invention set forth in the claims.

What is claimed is:
1. A method of making an implantable multicontact electrode array comprising:
  helically winding a plurality of insulated wires to define a lumen; each of said wires having a distal end;
  positioning a tube jacket around the helically wound wires, said tube jacket covering all but the distal end of the insulated wires;
  defining a pattern of marks on a metal foil carrier at a desired spacing and orientation using a positioning tool, which marks are used to define a pattern of spaced-apart distal electrodes to be included at a distal end of the multicontact electrode array;

welding respective electrode contacts to the marked locations on the metal foil carrier using a positioning tool and relying on the location marks scribed on the surface of the metal foil carrier;

electrically and mechanically attaching the distal end of each wire to a respective electrode contact;

forming the metal carrier into a tube, with the electrode contacts and wires residing on the inside of the foil tube;

placing heat-shrinkable tubing over the foil tube;

causing the heat-shrinkable tubing to shrink tightly around the outside of the foil tube;

injecting a liquid polymer into the inside of the foil tube to fill all gaps therein, and allowing said liquid polymer to cure;

mechanically removing the heat-shrinkable tubing; and removing the metal foil using an etching process, thereby exposing a surface of the electrode contacts that was previously held against the metal foil, said exposed surface of each electrode contact providing a distal electrode of the multicontact electrode array, wherein the distal electrodes are spaced apart and oriented using spacing tools and the markings on the metal foil.

2. The method of claim 1 wherein causing the heat-shrinkable tubing to shrink tightly around the foil tube comprises applying heat to the heat-shrinkable tubing.

3. The method of claim 2 further including trimming the distal tip of the heat-shrinkable tubing and foil tube after causing it to shrink tightly around the foil tube.

4. The method of claim 1 wherein electrically and mechanically attaching the distal end of each wire to a respective electrode contact comprises folding a portion of each metal contact over a distal tip of the wire, thereby mechanically holding the distal tip of the wire, and then welding the distal tip of the wire to the metal contact, thereby electrically attaching the wire to the metal contact.

5. The method of claim 1 wherein electrically and mechanically attaching the distal end of each wire comprises welding in a sandwich configuration a distal end of the wire between two layers of soft metal foil.

6. The method of claim 1 wherein removing the heat-shrinkable tubing comprises mechanically cutting and peeling off the heat-shrinkable tubing.

7. The method of claim 1 wherein removing the metal foil comprises chemically etching the metal foil away.

8. The method of claim 7 wherein chemically etching away the metal foil comprises inserting metal foil tube into an acid mixture.

9. The method of claim 8 further including elevating the temperature of the acid mixture to at or near its boiling point and inserting the metal foil tube in the acid mixture for about 1–5 minutes.

10. The method of claim 1 wherein welding respective electrode contacts to the marked locations on the metal foil carrier comprises welding respective metal strips to the marked locations on the metal foil carrier, said metal strips forming at least a segment of a ring electrode once the metal foil carrier has been formed into the foil tube.

11. The method of claim 3 wherein forming the metal foil carrier into a foil tube, with the electrode contacts and wires residing on the inside of the foil tube, comprises drawing the metal foil carrier through a die.

12. The method of claim 11 further including placing a removable plug in the lumen defined by the helically wound wires prior to injecting the liquid polymer into the inside of the foil tube.

13. The method of claim 12 further including extending the removable plug into the body of the foil tube prior to injecting the liquid polymer into the inside of the foil tube, whereby the remove plug when removed defines a lumen within that portion of the distal end of the electrode array whereat the electrodes reside.

14. The method of claim 11 wherein defining a pattern of marks on the metal foil carrier comprises using a positioning tool to make marks on the metal foil carrier that are spaced apart a distance L7, thereby causing the electrode contacts to be spaced-apart a distance L7.

15. The method of claim 14 wherein the distance L7 comprises about 2 mm.

16. A method of making a multicontact electrode array comprising:

(a) preparing a multiwire lead by helically winding the wires to define a lumen, placing the helically-wound wires inside a tube jacket, and forming at a distal end of each wire a pigtail end that is bent radially out from a center of the lumen to facilitate electrical connection therewith;

(b) defining a pattern of marks on a foil metal carrier to define electrode placement locations;

(c) bonding an electrode contact to the foil metal carrier at each defined location;

(d) electrically and mechanically bonding the pigtail end of each wire to a respective electrode contact;

(e) forming the foil metal carrier into a foil tube having a round or elliptical cross section, with the electrode contacts and wires secured to the inside surface of the tube;

(f) filling the inside of the foil tube with a polymer;

(g) trimming excess material from a distal end of the polymer-filled foil tube; and (h) etching away the foil tube to expose the electrode contacts at a distal end of the electrode array.

17. The method of claim 16 wherein filling the inside of the foil tube with a polymer comprises placing a heat-shrink tube around the foil tube to seal the joining slit of the foil tube;

applying heat to the heat-shrink tube to cause it to shrink tightly around the foil tube;

injecting a liquid polymer into the foil tube; and curing the liquid polymer.

18. The method of claim 17 wherein removing the heat-shrink tube further comprises mechanically removing the heat-shrink tube by cutting the heat-shrink tube with a scalper tool and peeling the heat-shrink tube off.

19. The method of claim 17 wherein removing the foil tube further comprises removing the foil tube using a chemical etching process.

20. The method of claim 16 wherein electrically and mechanically bonding the pigtail end of each wire to a respective electrode contact comprises folding a portion of the electrode contact over the pigtail end to mechanically bond the wire to the electrode contact, and resistance welding the pigtail end to the folded electrode contact in a sandwich configuration between two layers of metal foil carrier.

21. The method of claim 16 wherein forming the foil metal carrier into a foil tube having a round or elliptical cross section comprises subjecting the foil metal carrier, with electrode contacts and wires bonded thereto, to a drawing die.

22. The method of claim 16 wherein preparing the multiwire lead by helically winding the wires to define a lumen comprises winding multiple wires on a mandrel in helical fashion, and removing the mandrel after the winding is complete.

* * * * *